United States Patent [19]

Mittenzwei et al.

[11] 4,116,948

[45] Sep. 26, 1978

[54] PROCESS FOR REMOVAL OF INORGANIC SALTS FROM PEPTIDE/SALT-CONTAINING SUBSTANCES

[75] Inventors: Hellmut Mittenzwei, Pixistrasse 10, 8000 Munich, Germany; Janez Terpin, Hohenbrunn, Germany

[73] Assignee: Hellmut Mittenzwei, Germany

[21] Appl. No.: 838,486

[22] Filed: Oct. 3, 1977

Related U.S. Application Data

[63] Continuation of Ser. No. 667,456, Mar. 16, 1976, abandoned.

[30] Foreign Application Priority Data

Mar. 24, 1975 [DE] Fed. Rep. of Germany ....... 2512936

[51] Int. Cl.$^2$ ............................................. C07G 7/00
[52] U.S. Cl. .................................... 260/112 R; 55/67; 55/386; 73/23.1; 73/421.5 R; 210/31 C; 210/198 C; 260/112 B
[58] Field of Search ............ 210/31 C, 198 C; 55/67, 55/197, 386; 73/23.1, 421.5; 260/112 R, 112 B

[56] References Cited

U.S. PATENT DOCUMENTS

| 3,078,647 | 2/1963 | Mosier | 55/60 |
|---|---|---|---|
| 3,856,669 | 12/1974 | Ito et al. | 210/31 C |

OTHER PUBLICATIONS

"A Method for Concentrating Solutes of High Molecular Weight"; Flodin et al.; Nature; Nov. 5, 1960, pp. 493, 494.

"Solid Phase Peptide Synthesis"; W. H. Freeman & Co.; Pubrs; 1969; pp. 50–52.

"Trennung von Proteinen und Peptide"; Determann et al.; Wiley Interscience Publn; vol. II, pp. 1052–1058; Chem Abs.; vol. 72, 1970, art No. 129360h.

*Primary Examiner*—Frank Sever
*Attorney, Agent, or Firm*—Hammond & Littell

[57] ABSTRACT

The invention concerns a process for removing inorganic salts from a liquid medium having a solids content of from about 25 to about 65 mg/ml and containing active organic peptide substances of a molecular weight of from about 500 to about 10,000 and up to 70% by weight inorganic salts based on the solids content of the liquid medium, which comprises the steps of transferring said liquid medium onto a filtration gel layer carried on a perforated centrifuge drum at a liquid medium: gel volume ratio of from about 1:2.5 to about 1:4.5, said filtration gel layer being higher cross-linked and having a particle size of from about 40 to 120 $\mu$, centrifuging at a centrifugal force of from about 800 to about 1500 g, and collecting the liquid centrifugate containing the active organic peptide substances and a low amount of salt.

The substance recovered by the process possesses growth regulating properties and can be recovered from mammalian blood or serum.

7 Claims, No Drawings

PROCESS FOR REMOVAL OF INORGANIC SALTS FROM PEPTIDE/SALT-CONTAINING SUBSTANCES

This is a continuation of Ser. No. 667,456, filed Mar. 16, 1976, now abandoned.

The invention relates to a process for removing inorganic salts from a liquid peptide- and salt-containing medium having a total solids content of from about 25 to about 65 mg/ml, a content of active peptide substances having a molecular weight of from about 500 to about 10,000 and a content of up to 80% by weight of inorganic salts, calculated on the solids content of the liquid medium.

Many methods of separating higher molecular weight proteins or peptides from low molecular weight substances such as inorganic salts, are described in the chemical literature. The application of these techniques to the separation of low molecular weight peptides from low molecular weight substances have however led to anything but satisfactory results.

Thus, the dialysis and ultra-filtration methods are technically impractical for the region below 5,000 Dalton because of the low degree of separation. Ion exchange chromatography with synthetic resin ion exchangers cannot be employed because of the danger of irreversible denaturisation (F. Korte Methodicum Chimicum, Vo. 1, P. 1054, right hand column (1973)) and adsorption of the organic substances (J. M. STEWART u. J. D. YOUNG, Solid Phase Peptide Synthesis, P. 51 (1969), published by W. H. Freeman and Co., San Francisco). Also ion exchangers in which the carrier material is a polysacharide or cellulose matrix are unsuitable because of their relatively small capacity and very low flow-through rate (F. KORTE supra P. 1054, right hand column). Furthermore, all column chromatographic processes as well as gel filtration in a column are impractical on a technical scale, particularly in the removal of salts from a liquid medium having a high salt concentration, because of the association with large volumes of eluate.

Also, employment of modified separation processes, such as gel filtration in a centrifuge, provides no satisfactory results in these cases. Thus, one does not obtain useful results by centrifuge gel filtration employing a cross linked Dextran having a particle size of from about 30 to 150μ in the separation of salts from peptide type substances such as cytochrome C (Mol. weight of about 12,000). A major proportion of the activity remains in the gel and can only be recovered by extensive washing of the filtration gel [Flodin et al., Nature, 493 (1960)]. When dealing with low molecular weight peptides, this process is thus also not suitable. The reason for this is reported to be that properties such as charge and affinity play a greater and greater role as the size of the molecule decreases [F. Korte, supra, P. 1058, right hand column].

In the light of knowledge of the above works, it was thus not considered that one of the methods mentioned would be suitable for separating inorganic salts from particular liquid mediums having a high inorganic salt content (up to 80% by weight, calculated on the solids content of the liquid medium) and a low content of low molecular weight peptides or proteins (Mol. weight up to 10,000). All techniques employed in extensive experimentation proved to be very time consuming, and the peptide could only be obtained in low concentration in large volumes of liquid. Employment of centrifuge gel filtration for the above liquid mediums however surprisingly produced very satisfactory results when maintaining particular conditions.

It was found that by controlling various parameters, particularly liquid medium: gel volume ratio, the degree of cross-linking and particle size of the filtration gel, and also the centrifugal force applied, inorganic salts can be very satisfactorily removed and a surprisingly high percentage of active low molecular weight peptide substance recovered.

The process of the abovementioned type is, in accordance with the invention, thus characterised by transferring the liquid medium onto a filtration gel layer carried on a perforated centrifuge drum at a liquid medium: gel volume ratio of from about 1:2.5 to about 1:4.5, said filtration gel layer being highly cross-linked and having a particle size of from about 40 to about 120μ, centrifuging at a centrigugal force of from about 800 to about 1500 g, and collecting the liquid centrifugate containing the active organic peptide substances and a low amount of salt.

The liquid medium is most conveniently transferred to the filtration gel while the centrifuge drum is rotating with a centrifugal force of from about 10 to about 80 g, preferably about 60 g. The rate of rotation of the centrifuge drum is then increased until the centrifugal force is achieved.

Washing out with eluent of the active organic peptide substances remaining on the filtration gel layer, while centrifuging at the same centrifugal force of from about 800 to about 1500 g, may then be effected, and the eluate containing the active organic peptide substances collected. The eluate may then be concentrated by vacuum distillation at from about 20° to about 40° C. to a solids content of from about 25 to about 65 mg/ml, and the concentrated liquid may again be subjected to the above process for removing inorganic salts.

The low salt containing liquid collected from this procedure is then employed to produce an isotonic solution of the active peptide substances containing less than 25% by weight of inorganic salts based on the solids content of the isotonic solution, which is then advantageously concentrated to a solids content of about 18 mg/ml.

The process of the invention is particularly suitable for separating inorganic salts from a liquid peptide- and salt-containing medium which has been obtained from a deproteinated extract from fresh mammalian blood or serum, such as human or preferably calf blood or serum and which has a total solids content of from about 25 to about 65 mg/ml, active peptide substances having a molecular weight of from about 500 to about 10,000, and up to 80% by weight of inorganic salts, calculated on the solids content of the liquid medium. The process of the invention furthermore, allows for separation, particularly of inorganic salts from a liquid peptide-and-salt containing medium of the above composition, in which more than 90% by weight of the active peptide substances are of a molecular weight of below 5,000.

The invention extends to an isotonic solution of active organic peptides containing less than 25% by weight of inorganic salts based on the solids content of the isotonic solution, produced by the process described for obtaining such, particularly the isotonic solution obtained from liquid medium which has been obtained from a deproteinated extract from mammalian blood or serum.

It is known that substances having growth regulating properties can be recovered from mammalian blood or serum. For example, peptides recovered from the blood of animals by the procedure described in German Pat. No. 1,076,888 are known to possess such properties. This product (liquid medium) may have a solids content of from about 20 to 65 mg/ml and contains active organic peptide substances of a molecular weight in the region of 3000 and lower and furthermore up to 70% by weight of inorganic salts, based on the solids content of the liquid medium. Each ml of this known product possesses an insulin-like activity of about 10 to 15 $\mu$U/mg (micro International unit for insulin or insulin-like activity per milligram) and is employed in an injectable solution having a solids content of about 40 mg/ml particularly for accelerating and influencing healing processes. Dosages employed are dependent on the mode of application and the nature and severity of the condition being treated. The types of wounds which may be treated include burns, ulcers, decubitus and the like, and application of the product may i.v., i.a., i.m., (intravenous, intraartereal and intramuscular, respectively) or topical in the case of open wounds. Therapy by injection, such as in treating internal ulcers in man, for example, involves initial i.v. or i.a. daily doses of 200 to 800 mg of the product and subsequent treatment with daily doses of 80 to 200 mg administered i.v., or i.m. This injectable solution is hypertonic at the requisite concentration, and in the therapeutic use of this product, the electrolytes contained therein in high concentration can lead to a disturbance of the electrolyte level in the body or to local irritation. As shown by figures reported in the examples, the inorganic salts comprise a large amount of potassium ions, amongst others, which increases the therapeutic risk of the medicament. In certain circumstances it can lead to hyperkalemic symptoms such as muscle weakness, influence on breathing and most importantly a influence on the heart function. The products produced by the above process such as the isotonic solution described in the examples, on the other hand now have a content of less than 25% by weight of inorganic salts calculated on the solids content of the isotonic solution, and thus have, amongst others, a significantly lower potassium concentration. 1 ml of the isotonic solution having a solids content of about 18 mg/ml corresponds in activity to the above-mentioned known products having a solids content of about 40 mg/ml, and one can employ this substance in the same manner for the same indications at the correspondingly lower doses.

EXAMPLE 1

To a G 3 glass filter insert contained in a centrifuge glass (6,4 × 11cm) 62 ml of a hydrated copolymer of ethyleneglycoldimethacrylate and a polyethyleneglycoldimethacrylate having a particle size from 63 to 100$\mu$ (Merckogel PGM-2000) is added and then centrifuged for 10 minutes at about 1000 g in a Stock beaker centrifuge, whereby an even gel layer is formed. Onto this gel layer, 25 ml of a peptide- and salt- containing blood extract of different concentrations (25-65 mg/ml), see Table 1, is evenly transferred with a pipette and the solution is then allowed to sink into the gel layer. Centrifuging is then effected as above for 10 minutes, whereby one obtains about 25 ml of low salt content peptide-containing centrifugate. The gel layer is subsequently washed five times with 30 ml each of distilled water by transferring the water with a pipette and then centrifuging at 1000 g. The combined wash water is concentrated in a rotation concentrator at 30° C. under vacuum to 25 ml. and the concentrate is then transferred to the centrifuge dried gel layer and centrifuged as above. The centrifugate thus obtained is then combined with the low salt content centrifugate of the first separation and concentrated by vacuum distillation at 30° C. to a solids content of about 18 mg/ml. The dependence of the degree of desalting and the yield of organic components on the concentration of the extract to be desalted at a constant volume ratio of extract to gel of 1:2,5 can be seen from Table I.

Table I

| Experiment number | Concentration (mg/ml) | Degree of desalting (%) | Yield of organic substance (%) |
|---|---|---|---|
| 1 | 25 | 64 | 73 |
| 2 | 35 | 60,4 | 77,2 |
| 3 | 45 | 60,2 | 73,2 |
| 4 | 55 | 53,4 | 75,6 |
| 5 | 65 | 49,8 | 69 |

EXAMPLE 2

50 g of a copolymer of dextran and epichlorhydrin having a particle size of 40 to 120$\mu$ (Sephadex G-10) is allowed to expand in a conventional amount of water and the resulting aqueous suspension poured into a G 3 glass filter insert located in a centrifuge glass (6,4 × 11 cm) and then the whole is centrifuged for 10 minutes at 1000 g in a Stock beaker centrifuge. An even gel layer of about 115 ml volume is formed. Different volumes (25-45 ml, see Table II) of a peptide- and salt- containing blood extract having a constant dry weight of 45 mg/ml is then evenly transferred onto this gel layer with a pipette. After the solution has sunk into the gel bed, centrifuging for 10 minutes at about 1000 g is effected. The low salt content peptide-containing centrifugate produced thereby is collected. For a quantitative elution of the active peptide substances remaining in the gel layer, the gel layer is washed five times with 30 ml of water by transferring the water to the gel layer with a pipette and centrifuging at 1000 g. The combined wash water is concentrated in a rotation concentrator at 30° C. under vacuum to a solids content of 45 mg/ml, and the concentrate is then transferred onto the centrifuge dried gel layer and centrifuged as described above. The centrifugate obtained is combined with the centrifugate of the first separation process and is concentrated by vacuum distillation at 30° C. to a solids content of about 18 mg/ml.

The dependence of the degree of desalting and the yield of the organic components on the volume ratio of liquid medium to gel layer at a constant concentration of 45 mg/ml can be seen from table II.

Table II

| Experiment number | Extract volume of gel volume | Degree of desalting (%) | Yield of organic substance (%) |
|---|---|---|---|
| 1 | 1 : 2,5 | 35.2 | 62 |
| 2 | 1 : 3,5 | 48,6 | 70 |
| 3 | 1 : 4 | 65 | 73,2 |
| 4 | 1 : 4,5 | 80 | 78 |

EXAMPLE 3

An aqueous suspension of 2,9 l of a copolymer ethyleneglycoldimethacrylate and a polyethyleneglycoldimethacrylate having a particle size of from 63–100μ (Merckogel PGM-2000) or 2,3 kg of a copolymer of dextran and epichlorhydrin having a particle size of from 40 to 120μ (Sephadex G-10) expanded in water is poured portion-wise into a Heine-universal-centrifuge EO, in which the drum is fitted with a filter, at a rotation speed of about 200 g. In order to form as even a gel layer as possible, about ten liters of water is then added at the same rotation speed. By then centrifuging at 1000 g, the water situated between the gel particles is removed. Onto this gel layer a total of 1250 ml of a peptide- and salt- containing blood extract having a dry weight of 45 mg/ml and about 70% inorganic parts, calculated on the dry mass, is then transferred with the aid of a spray nozzle (nitrogen serves as propellant; pressure about 3 kg/cm$^2$) under rotation of the centrifuge drum at 60 g. After about 5 minutes, the speed is increased to 1000 g and so maintained until no further liquid issues from the centrifuge. One achieves about 1250 ml of low salt content centrifugate having a dry weight of about 8 mg/ml and about 20% inorganic parts. The gel layer is washed five times with 1250 ml of distilled water (transferred at 60 g and centrifuged at 1000 g) and the combined wash water is then concentrated to 1200 ml in a rotation concentrator at 30° C. under vacuum and then newly centrifuged as described above. This centrifugate having a dry weight of about 5 mg/ml and about 24% inorganic parts is combined with the centrifugate of the first separation procedure and concentrated by vacuum distillation at 30° C. to about 18 mg/ml. In this manner one obtains an isotonic solution of the active peptide substances having an inorganic salt content of less than 25%, calculated on the dry substance, and an insulin-like-activity of 20–25 μU/mg.

In table III there is provided analytical data on some of the important components comprised in the desalted solution obtained by Example 3, as compared to the starting solution.

Table III

| Sample | Na$^+$ (%) | K$^+$ (%) | Cl (%) | PO$_4$ (%) | L-Lactat (%) | Amino nitrogen (%) | Peptide Content +) (TLC |
|---|---|---|---|---|---|---|---|
| Starting liquid medium | 27,8 | 4,57 | 34 | 3,15 | 6,7 | 0,46 | iden- |
| Combined centrifugate | 15 | 1,42 | 13,3 | 1,06 | 11,7 | 1,68 | tical |

+) TLC - determined by thin layer chromatography

What is claimed is:

1. A process for removing inorganic salts from a liquid medium having a solids content of from about 25 to about 65 mg/ml and which contains active organic peptide substances of a molecular weight of from about 500 to about 10,000 and a high amount up to 70% by weight of inorganic salts based on the solids content of the liquid medium, which comprises the steps of transferring said liquid medium onto a filtration gel layer carried on a perforated centrifuge drum at a liquid medium: gel volume ratio of from about 1:2.5 to about 1:4.5, said filtration gel layer being highly cross-linked and having a particle size of from about 40 to about 120μ, centrifuging at a maximum centrifugal force of from about 800 to about 1500 g, and collecting the liquid centrifugate which contains the active organic peptide substances and an amount of salt reduced by 32.2 to 80% of said high amount.

2. A process according to claim 1, in which the liquid medium is transferred onto the filtration gel layer, while the centrifuge drum is rotating with a lesser centrifugal force of from about 10 to about 80 g and then the speed of rotation is increased to said maximum centrifugal force.

3. A process according to claim 1, which comprises the further steps of washing out with eluent active organic peptide substances remaining on the filtration gel layer after centrifuging, while centrifuging at said maximum centrifugal force of from about 800 to about 1500 g, and collecting the liquid eluant which contains the active organic peptide substances.

4. A process according to claim 3, in which collected eluate which contains the active organic peptide substances is concentrated by vacuum distillation at from about 20 to about 40° C. to a solids content of from about 25 to about 65 mg/ml, and in which the concentrated liquid is transferred onto a filtration gel layer carried on said perforated centrifuge drum.

5. A process according to claim 1, in which the collected liquid resulting from claim 1 which contains the active organic peptide substances is concentrated to a solids content of about 18 mg/ml, whereby an isotonic solution of the active organic peptide substances is obtained which contains less than 25% by weight of inorganic salts based on the solids content of the isotonic solution.

6. A process according to claim 1, in which the liquid medium has been obtained from a deproteinated extract from mammalian blood or serum.

7. A process according to claim 6, in which more than 90% by weight of the active organic peptide substances is of a molecular weight less than 5,000.

* * * * *